(12) United States Patent
Yang et al.

(10) Patent No.: US 10,183,028 B2
(45) Date of Patent: Jan. 22, 2019

(54) **ENRICHMENT METHOD OF ERGOSTEROL PEROXIDE FROM SPORODERM-BROKEN *GANODERMA LUCIDUM* SPORE POWDER**

(71) Applicants: Guangzhou Polysarm Bioscience Corp., Guangzhou (CN); Guangdong Yuewei Edible Fungi Technology Co., Ltd., Guangzhou (CN)

(72) Inventors: Burton B. Yang, Guangzhou (CN); Yizhen Xie, Guangzhou (CN); Chunwei Jiao, Guangzhou (CN); Ou Shuai, Guangzhou (CN); Xiangmin Li, Guangzhou (CN)

(73) Assignees: Guangdong Yuewei Edible Fungi Technology Co, Ltd., Guangzhou (CN); Guangzhou Polysarm Bioscience Corp., Guangzhou (CN)

( * ) Notice: Subject to any disclaimer, the term of this patent is extended or adjusted under 35 U.S.C. 154(b) by 4 days.

(21) Appl. No.: 15/526,682

(22) PCT Filed: Dec. 1, 2015

(86) PCT No.: PCT/CN2015/096082
§ 371 (c)(1),
(2) Date: May 12, 2017

(87) PCT Pub. No.: WO2017/028397
PCT Pub. Date: Feb. 23, 2017

(65) Prior Publication Data
US 2017/0360802 A1    Dec. 21, 2017

(30) Foreign Application Priority Data

Aug. 20, 2015 (CN) .......................... 2015 1 0512672

(51) Int. Cl.
| | |
|---|---|
| *A23G 4/00* | (2006.01) |
| *A61K 31/56* | (2006.01) |
| *A61K 36/074* | (2006.01) |
| *C07J 71/00* | (2006.01) |
| *A61K 36/00* | (2006.01) |

(52) U.S. Cl.
CPC ............ *A61K 31/56* (2013.01); *A61K 36/074* (2013.01); *C07J 71/0005* (2013.01); *A23G 4/00* (2013.01); *A61K 36/00* (2013.01)

(58) Field of Classification Search
None
See application file for complete search history.

(56) References Cited

PUBLICATIONS

Yuan et al (J. Agric. Food Chem., 54:6172-6176, 2006).*

\* cited by examiner

*Primary Examiner* — Brian Gangle
(74) *Attorney, Agent, or Firm* — Wang Law Firm, Inc.

(57) ABSTRACT

The invention provides an enrichment method of Ergosterol peroxide from sporoderm-broken *Ganoderma lucidum* spore powder, comprising the steps of preparing crude extract containing Ergosterol peroxide, purification by medium pressure preparative chromatography, purification by simulated moving-bed, and recrystallization. The operation of this invention is simple and stable, with higher yield and low cost, suitable for industrial-scale production.

15 Claims, No Drawings

ENRICHMENT METHOD OF ERGOSTEROL PEROXIDE FROM SPORODERM-BROKEN *GANODERMA LUCIDUM* SPORE POWDER

TECHNICAL FIELD

This invention relates to an enrichment method of Ergosterol peroxide, in particular to an enrichment method of Ergosterol peroxide from sporoderm-broken *Ganoderma lucidum* spore powder, belonging to the field of extraction-separation.

BACKGROUND

Ergosterol peroxide, with the full name of $5\alpha,8\alpha$-Epidioxyergosta-6,22-dien-3$\beta$-ol, is a known compound, belonging to the sterols, widely existing in edible-medicinal fungus or other fungus. There are many reports about its activities; for example, Chinese patent application No. 201410311586.3 discloses that it has synergy with taxol in killing or damaging Hela cancer cells, reducing the side effects of chemotherapy and its cost by reducing the necessary dosage of taxol. Chinese application No. 200610126091.9 discloses that ergosterol peroxide has significant anti-tumor (human breast cancer and liver cancer) pharmacological activity, and has no harmful effects on immune organs and weight. Chinese application No. 201210233192.1 reported that it has significant inhibitory effect on malignant breast cancer cells (MT-1), lymphoma cancer cells (Jurkat) and brain tumor cells (U87), and kills drug-resistant brain tumor stem cells. Chinese application No. 200810119948.3 reported that ergosterol peroxide has remarkable antifungal bioactivity and can be used in the field of natural antibiotics. Chinese application No. 01817014.5 disclosed that ergosterol peroxide has strong inhibitory effects on the formation of melanin and can be used in the field of whitening cosmetics. Chinese application No. 01817014.5 disclosed that ergosterol peroxide has poisoning effects on agricultural pests, such as *pieris rapae, prodenia litura*, aphid and so on, and is therefore applicable to the field of pesticides. In addition, ergosterol peroxide is reported in other literature to have extensive pharmacological actions, such as antioxidation, antituberculosis, anti-inflammation, anti-atherosclerosis, inhibiting the proliferation of T-cells, and so on.

There are fewer reports on the methods of extraction, separation and purification of ergosterol peroxide, which was identified from isolated unknown monomers in most reports, and in a fraction of these reports some authors still misjudge it altogether. Chinese application No. 201210233192.1 broke the sporoderm of *Ganoderma lucidum* spore powder by the enzyme method and obtained the extract by the supercritical carbon dioxide extraction method. Tracing activity by the tumor inhibitory rate, a single monomer with highest activity, which was identified as ergosterol peroxide, was obtained by three times positive silica gel column chromatography with chloroform, ethyl acetate, petroleum ether-ethyl acetate as eluent in sequence, and followed by preparative chromatography. Using *Naematoloma fasciculare* fruit body and mycelium as materials, Chinese application No. 201210233192.1 disclosed obtaining two monomers by extracting with methyl alcohol and petroleum ether in turn, positive silica gel column chromatography with cyclohexane-ethyl acetate as eluent, and recrystallizing several times; one of the monomers was identified as ergosterol peroxide. In Chinese application No. 200810119948.3, a petroleum ether fraction from the fermented liquid of fungus Ppf4 and another petroleum ether fraction from the acetone extract of hypha were merged; three monomers were obtained by positive silica gel column chromatography with cyclohexane-acetone as eluent, followed by gel column and reversed silica gel column chromatography; one of the monomers was identified as ergosterol peroxide. Using the fruit body of *Ganoderma lucidum* as material, Cheng Chunru ("Chemical constituents from the fruiting body of *Ganoderma lucidum* with cytotoxicity investigations", Journal of Shenyang Pharmaceutical University, 2014, 31(2): 102-106) obtained a fraction by extraction with 95% ethanol, extraction with petroleum ether, and positive silica gel column chromatography with petroleum ether-ethyl acetate as eluent; removing a monomer with recrystallization, another monomer was obtained finally by semi-preparative isolation from the mother liquid and identified as ergosterol peroxide. Using *Shiraia bambusicola* as material, Liu Yafeng, et al. ("Separation of peroxy-ergosterol in fungus" Zhuhuang, Journal of Tianjin University of Traditional Chinese Medicine, 2004, 23(1): 15-16) obtained a monomer, which was identified as ergosterol peroxide, by extracting several times with ethyl acetate and positive silica gel column chromatography. Zhang Nengsheng et al. ("Isolation and Purification of Peroxy-ergosterol from *Paecilomyces fumosoroseus* by High-Speed-Counter-Current Chromatography and identification by ESI-MS", Food and Fermentation Industries, 2009, 35(6): 14-16) studied the isolation and purification of peroxy-ergosterol from *paecilomyces fumosoroseus* by advanced high-speed-counter-current chromatography, but the obtained target product is actually not peroxy-ergosterol, because the obtained target has no UV absorption at 240-400 nm, while 280 nm was used as UV absorption wavelength to detect the process of isolation and to test the purity in the report, and the chromatogram showed a larger absorbency. The author may have made a mistake.

The above-mentioned techniques of separation and purification of ergosterol peroxide have something in common: extraction with neutral or strong polarity organic solvent at first, then removing impurities by extraction for several times with weak polarity organic solvent, followed by several rounds of positive silica gel column chromatography repeatedly with weak polarity organic solvent having a certain ratio as eluent, collecting the target fractions, and then obtaining the monomer of ergosterol peroxide by the steps of gel chromatography, preparative chromatography, recrystallization and so on; the yields of ergosterol peroxide are mostly in milligrams, and the processes started without a known destination, that is, the monomer was obtained at first, and then was identified as ergosterol peroxide later. Preparation was meant to discover the chemical composition of natural plants and fungi without an intended definite end result; accordingly, the preparation process proved complex and varied with little consideration for cost and yield. Furthermore, the preparation process involved toxic reagents without regard for environmental safety. In summary, the above mentioned techniques are not suitable for direct application in industrial production.

The simulated moving bed chromatography separation system is the organic combination of simulated moving-bed technology and chromatographic separation technology. The efficiency of a moving bed is simulated by adopting chromatographic columns in serial connection while an electromagnetic valve permits continuous switching between inlet and outlet, allowing the stationary phase to circulate with a continuous countercurrent. The combination of simulated moving-bed and chromatography changed chromatographic separation from a discontinuous into a continuous process, allowing large output, high yield, and high purity, and has been applied in the field of petroleum and chemicals, food, fermentation, medicine and so on, mainly in the purification of petrochemicals, saccharide, fermented product, active components in traditional Chinese medicine, and chiral compounds. But there are yet no reports about purification of ergosterol peroxide by using simulated moving-bed technology.

CONTENTS OF THE INVENTION

To alleviate the drawbacks of the prior art, the object of this invention is to provide an industrial-scale enrichment method of Ergosterol peroxide from sporoderm-broken *Ganoderma lucidum* spore powder having simple and stable operation, higher yield and low cost.

In order to achieve the above mentioned objects, the technical attributes of this invention are as follows:

An enrichment method of Ergosterol peroxide from sporoderm-broken *Ganoderma lucidum* spore powder comprising the following steps:

(1) Preparing crude extract containing Ergosterol peroxide: taking the sporoderm-broken *Ganoderma lucidum* spore powder, performing extraction by percolation or reflux method, concentrating the extract liquid to dryness under reduced pressure, and obtaining a crude extract A containing Ergosterol peroxide;

(2) Purification by medium pressure preparative chromatography: dissolving the crude extract containing Ergosterol peroxide prepared in step (1) with 60-95% methanol aqueous solution to obtain the sample solution for medium pressure preparative chromatography, performing purification by medium pressure preparative chromatography, collecting the fraction containing Ergosterol peroxide, concentrating it to dryness under reduced pressure to obtain the extractum B containing Ergosterol peroxide;

(3) Purification by simulated moving-bed: dissolving the extractum B containing Ergosterol peroxide prepared in the step (2) with 60-95% methanol aqueous solution to obtain the sample solution, injecting the sample solution into the simulated moving-bed chromatography separation system for further purification, concentrating the extract liquor containing Ergosterol peroxide to dryness under reduced pressure, and obtaining the dry extract C rich in Ergosterol peroxide; and (4) Dissolving the dry extract C rich in Ergosterol peroxide prepared in the step (3) with ethyl acetate-cyclohexane under heating conditions, transferring it into an environment at a temperature of 0-8° C. for recrystallization, filtering and washing the precipitate to obtain Ergosterol peroxide with high purity.

The extraction solvent of percolation or reflux method in step (1) is one of ethyl acetate, ethyl acetate-cyclohexane, and cyclohexane petroleum ether, or a mixture of them with any ratio.

The said percolation in step (1), wherein, the immersing time is 24-48 h, the immersing temperature is room temperature, and percolate is collected at approximate to constant speed for 5-10 bed volume.

The said reflux method in step (1), wherein, the liquid-solid ratio is 6:1 to 10:1, the extracting time at boiling condition is 1-2 h, the residue is repeatedly extracted, and the filtrates are merged together.

The said step (2), wherein, the medium pressure preparative chromatography column is packed with 30-50 µm octadecylsilyl silica gel, the height of the column is 45 cm, the solid content of sample solution is 0.05-0.2 g/mL, the injection rate is 2-5 mL/min and the injection volume is 0.1 bed volume, performing isocratic elution with 60-95% methanol aqueous solution at the rate of 1.2-2.0 bed volume per hour.

The said step (3), wherein, the solid content of the sample solution is 0.05-0.2 g/mL, the simulated moving-bed chromatography system uses octadecylsilyl reversed silica gel with particle size of 30-50 µm as packing materials, the system is divided into four areas, adopting 8-16 columns in series connection, each of which has 2-4 columns in series connection, and the system parameters are set up as follows: room temperature, flow rate of injection pump is 3-6 mL/min, flow rate of elution pump is 16-38 mL/min, extraction velocity is 10-23 mL/min, flow rate for raffinate is 9-21 mL/min, and switching time is 10-24 min.

The said step (4), wherein, the dosage of ethyl acetate-cyclohexane is 10-20 times that of the dry extract C, the volume ratio of ethyl acetate to cyclohexane is 50:50-10:90, and the time of recrystallization is 36-48 h.

Compared with the extract methods of ergosterol peroxide in prior art, the present invention has the advantages of:

(1) The medium pressure preparative chromatography in this invention plays a function of removing impurities and enrichment, having no new impurities and toxic or harmful substances introduced, maintaining the natural quality of ergosterol peroxide well, and being good and safe for the environment, as compared to prior existing processes. Both the yield and content of ergosterol peroxide in the obtained extractum are higher, due to better effects in removing impurities. Therefore it is more suitable for being pretreatment of the enrichment process by simulated moving-bed chromatography.

(2) The present invention performs further purification by simulated moving-bed chromatography. The combination of simulated moving-bed and chromatography changes chromatographic separation from a discontinuous into a continuous process and retains the advantages of chromatographic separation, such as excellent separation efficiency, low-energy, low-material consumption, operation at room temperature and so on. The stationary phase and mobile phase can be repeatedly applied, efficiency is raised greatly, and cost is reduced, due to the simulated countercurrent. Simulated moving-bed chromatography, in which the fractions are acquired from the beginning and end of the bands, makes the extraction process easily controlled; separation capability is enhanced and yield is increased, due to introducing rectification and reflux systems; productivity is increased, automation level and efficiency are enhanced, solvent wastage is reduced, and the production environment is improved greatly, due to the introduction of a continuous system.

(3) The purity of ergosterol peroxide, obtained by primary extraction, purification with medium pressure preparative chromatography, and enrichment with simulated moving-bed chromatography, is 50-80% in the present invention, which is higher than existing art.

EXAMPLES

The examples below further illustrate the invention, rather than limiting the scope thereof. The related methods and materials in this invention use conventional methods and materials commercially available, unless specially stated otherwise.

Example 1

Acquiring ergosterol peroxide from sporoderm-broken *Ganoderma lucidum* spore powder by the following steps:

(1) Preparing crude extract containing Ergosterol peroxide: taking the sporoderm-broken *Ganoderma lucidum* spore powder, performing extraction by percolation, of which the extraction solvent is ethyl acetate, the immersing time is 40 h at room temperature, and percolate is collected at approximate constant speed for 8 bed volume; concentrating the extract liquid to dryness under reduced pressure by rotary evaporator, the bathing temperature at 65° C., and the vacuum degree below −0.085, and obtaining the crude extract A with an ergosterol peroxide content of 0.62% revealed by the test results.

(2) Purification by medium pressure preparative chromatography: dissolving the crude extract A containing Ergosterol peroxide prepared in step (1) with 60% methanol aqueous solution by heating and ultrasonic vibration, filtrating the solution with 0.45 μm millipore filter to obtain the sample solution for medium pressure preparative chromatography, of which the solid content is 0.05 g/mL; performing purification by medium pressure preparative chromatography, of which the medium pressure preparative chromatography column is packed with 50 μm octadecylsilyl silica gel, the height of the column is 45 cm, the injection rate is 2 mL/min, and the injection volume is 0.1 bed volume, performing isocratic elution with 60% methanol aqueous solution at the rate of 1.2 bed volume per hour; collecting the fraction containing Ergosterol peroxide, concentrating it to dryness under reduced pressure by rotary evaporator, with the bathing temperature at 70° C., and the vacuum degree below −0.085, to obtain the extractum B with an Ergosterol peroxide content of 16.8%. In this step, the impurities with low polarity are almost removed entirely, and the impurities with high polarity are partly removed.

(3) Purification by simulated moving-bed: a simulated moving bed chromatography separation system includes an elution pump, an injection pump, an extracting pump, chromatographic columns, an electromagnetic valve, a check valve, a signal collector, a system controller, and so on. The flow rate of both the elution pump and the extracting pump are 0-250 mL/min, that of the injection pump is 0-50 mL/min, the operating pressures and operating temperatures of the three pumps are respectively 0-10 MPa and 15-35° C. The system, using octadecylsilyl reversed silica gel with particle size of 30 μm as packing materials, adopting 16 columns in series connection, is divided into four areas, each having 4 columns in series connection. The inlet and outlet positions can be changed at intervals by switching the electromagnetic valve, thus simulating moving of the separated bed. Dissolving the extractum B containing Ergosterol peroxide prepared in step (2) with 95% methanol aqueous solution by heating and ultrasonic vibration, filtrating the solution with 0.45 μm millipore filter to obtain the sample solution, of which the solid content is 0.2 g/mL; injecting the sample solution into the simulated moving-bed chromatography separation system for further purification. The system parameters are set up as follows: room temperature, the flow rate of the injection pump is 3 mL/min, the flow rate of the elution pump is 16 mL/min the flow rate of raffinate is 9 mL/min, and the switching time is 24 min, concentrating the extract liquor containing Ergosterol peroxide to dryness under reduced pressure by rotary evaporator, the bathing temperature is at 70° C., and the vacuum degree below −0.085, to obtain the dry extract C rich in Ergosterol peroxide.

(4) Dissolving the dry extract C rich in Ergosterol peroxide prepared in step (3) with ethyl acetate-cyclohexane under heating conditions, transferring it into an environment at a temperature of 0° C. for recrystallization, filtering and washing the precipitate to obtain Ergosterol peroxide with a purity of 53.7%. In this step, the dosage of ethyl acetate-cyclohexane is 20 times that of the dry extract C, the volume ratio of ethyl acetate to cyclohexane is 10:90, and the time of recrystallization is 40 h.

In this example, the content of Ergosterol peroxide is tested by HPLC-ESLD, and the chromatographic conditions are as follows: Agilent 1200 Series High Performance Liquid Chromatography (HPLC) System, Chromachem evaporative light-scattering detector (ELSD) from ESA company in America, Waters Symmetry Shield RP18 columns (4.6×250 mm, 5 μm), 90% acetonitrile aqueous solution as the mobile phase, isocratic elution, flow rate: 0.8 mL/min, column temperature: 30° C., temperature of drift tube: 80° C., temperature of atomizer: 60° C., nitrogen pressure: 25 psi, gain: 3, injection volume: 20 μL, purity calculation by external standard method.

Example 2

Acquiring ergosterol peroxide from sporoderm-broken *Ganoderma lucidum* spore powder by the following steps:

(1) Preparing crude extract containing Ergosterol peroxide: taking the sporoderm-broken *Ganoderma lucidum* spore powder, performing extraction by reflux method, of which the extraction solvent is cyclohexane-petroleum ether (1:1), the liquid-solid ratio is 10:1, the extracting time at boiling condition is 2 h, the residue is repeatedly extracted, and the filtrates are merged with each other; concentrating the extract liquid to dryness under reduced pressure by rotary evaporator, the bathing temperature at 60° C., and the vacuum degree below −0.085, and obtaining the crude extract A with an ergosterol peroxide content of 0.98% revealed by the test results.

(2) Purification by medium pressure preparative chromatography: dissolving the crude extract A containing Ergosterol peroxide prepared in step (1) with 95% methanol aqueous solution by heating and ultrasonic vibration, filtrating the solution with 0.45 μm millipore filter to obtain the sample solution for medium pressure preparative chromatography, of which the solid content is 0.2 g/mL; performing purification by medium pressure preparative chromatography, of which the medium pressure preparative chromatography column is packed with 30 μm octadecylsilyl silica gel, the height of the column is 45 cm, the injection rate is 5 mL/min, and the injection volume is 0.1 bed volume, performing isocratic elution with 80% methanol aqueous solution at the rate of 2.0 bed volume per hour; collecting the fraction containing Ergosterol peroxide, concentrating it to dryness under reduced pressure by rotary evaporator, with the bathing temperature at 65° C., and the vacuum degree below −0.085, to obtain the extractum B with an Ergosterol peroxide content of 10.2%. In this step, the impurities with low polarity are almost removed entirely, and the impurities with high polarity are partly removed.

(3) Purification by simulated moving-bed: the simulated moving bed chromatography separation system includes an elution pump, an injection pump, an extracting pump, chromatographic columns, an electromagnetic valve, a check valve, a signal collector, a system controller, and so on, the flow rate of both the elution pump and the extracting pump are 0-250 mL/min, that of the injection pump is 0-50 mL/min, the operating pressures and operating temperatures of the three pumps are respectively 0-10 MPa and 15-35° C. The system, using octadecylsilyl reversed silica gel with particle size of 50 μm as packing materials, adopting 8 columns in series connection, is divided into four areas, each having 2 columns in series connection. The inlet and outlet positions can be changed at intervals by switching the electromagnetic valve, thus simulating moving of the separated bed. Dissolving the extractum B containing Ergosterol peroxide prepared in step (2) with 60% methanol aqueous solution by heating and ultrasonic vibration, filtrating the solution with 0.45 μm millipore filter to obtain the sample solution, of which the solid content is 0.05 g/mL; injecting the sample solution into the simulated moving-bed chromatography separation system for further purification. The system parameters are set up as follows: room temperature, the flow rate of the injection pump is 6 mL/min, the flow rate of the elution pump is 38 mL/min, extraction velocity is 23 mL/min, the flow rate of raffinate is 21 mL/min, and the switching time is 10 min; concentrating the extract liquor containing Ergosterol peroxide to dryness under reduced pressure by rotary evaporator, the bathing temperature is at 65° C., and the vacuum degree below −0.085, to obtain the dry extract C rich in Ergosterol peroxide.

(4) Dissolving the dry extract C rich in Ergosterol peroxide prepared in step (3) with ethyl acetate-cyclohexane under heating conditions, transferring it into an environment at a temperature of 8° C. for recrystallization, filtering and washing the precipitate to obtain Ergosterol peroxide with a purity of 66.3%. In this step, the dosage of ethyl acetate-cyclohexane is 10 times that of the dry extract C, the volume ratio of ethyl acetate to cyclohexane is 50:50, and the time of recrystallization is 48 h.

In this example, the method of testing the content of Ergosterol peroxide is the same as that in example 1.

Example 3

Acquiring ergosterol peroxide from sporoderm-broken *Ganoderma lucidum* spore powder by the following steps:

(1) Preparing crude extract containing Ergosterol peroxide: taking the sporoderm-broken *Ganoderma lucidum* spore powder, performing extraction by reflux method, of which the extraction solvent is ethyl acetate-cyclohexane (1:1), the liquid-solid ratio is 6:1, the extracting time at boiling condition is 1 h, the residue is repeatedly extracted, and the filtrates are merged with each other; concentrating the extract liquid to dryness under reduced pressure by rotary evaporator, the bathing temperature at 70° C., and the vacuum degree below −0.085, and obtaining the crude extract A with an ergosterol peroxide content of 1.23% revealed by the test results.

(2) Purification by medium pressure preparative chromatography: dissolving the crude extract A containing Ergosterol peroxide prepared in step (1) with 80% methanol aqueous solution by heating and ultrasonic vibration, filtrating the solution with 0.45 μm millipore filter to obtain the sample solution for medium pressure preparative chromatography, of which the solid content is 0.15 g/mL; performing purification by medium pressure preparative chromatography, of which the medium pressure preparative chromatography column is packed with 40 μm octadecylsilyl silica gel, the height of the column is 45 cm, the injection rate is 4 mL/min, and the injection volume is 0.1 bed volume, performing isocratic elution with 80% methanol aqueous solution at the rate of 1.8 bed volume per hour; collecting the fraction containing Ergosterol peroxide, concentrating it to dryness under reduced pressure by rotary evaporator, with the bathing temperature at 60° C., and the vacuum degree below −0.085, to obtain the extractum B with an Ergosterol peroxide content of 20.4%. In this step, the impurities with low polarity are almost removed entirely, and the impurities with high polarity are partly removed.

(3) Purification by simulated moving-bed: the simulated moving bed chromatography separation system includes an elution pump, an injection pump, an extracting pump, chromatographic columns, an electromagnetic valve, a check valve, a signal collector, a system controller, and so on, the flow rate of both the elution pump and the extracting pump are 0-250 mL/min, that of the injection pump is 0-50 mL/min, the operating pressures and operating temperatures of the three pumps are respectively 0-10 MPa and 15-35° C. The system, using octadecylsilyl reversed silica gel with particle size of 40 μm as packing materials, adopting 12 columns in series connection, is divided into four areas, each having 3 columns in series connection. The inlet and outlet positions can be changed at intervals by switching the electromagnetic valve, thus simulating moving of the separated bed. Dissolving the extractum B containing Ergosterol peroxide prepared in step (2) with 85% methanol aqueous solution by heating and ultrasonic vibration, filtrating the solution with 0.45 μm millipore filter to obtain the sample solution, of which the solid content is 0.15 g/mL; injecting the sample solution into the simulated moving-bed chromatography separation system for further purification. The system parameters are set up as follows: room temperature, the flow rate of the injection pump is 5 mL/min, the flow rate of the elution pump is 33 mL/min, extraction velocity is 20 mL/min, the flow rate of raffinate is 18 mL/min, and the switching time is 15 min; concentrating the extract liquor containing Ergosterol peroxide to dryness under reduced pressure by rotary evaporator, the bathing temperature is at 60° C., and the vacuum degree below −0.085, to obtain the dry extract C rich in Ergosterol peroxide.

(4) Dissolving the dry extract C rich in Ergosterol peroxide prepared in step (3) with ethyl acetate-cyclohexane under heating conditions, transferring it into an environment at a temperature of 4° C. for recrystallization, filtering and washing the precipitate to obtain Ergosterol peroxide with a purity of 79.63%. In this step, the dosage of ethyl acetate-cyclohexane is 15 times that of the dry extract C, the volume ratio of ethyl acetate to cyclohexane is 30:70, and the time of recrystallization is 36 h.

In this example, the method of testing the content of Ergosterol peroxide is the same as that in example 1.

The above are only preferred embodiments of the present disclosure and should not be used for limiting the present disclosure. For those skilled in the art, any modifications, equivalent replacements, improvements and the like within the spirit and principle of the present disclosure shall fall within the scope of protection of the present disclosure.

The invention claimed is:

1. An enrichment method of extracting Ergosterol peroxide from sporoderm-broken *Ganoderma lucidum* spore powder, comprising the following steps:

(1) Obtaining a crude extract containing Ergosterol peroxide: taking the sporoderm-broken *Ganoderma lucidum* spore powder, performing extraction with an extraction solvent by percolation or reflux method, concentrating a resultant extract liquid to dryness under reduced pressure, and obtaining the crude extract containing Ergosterol peroxide;

(2) Purification by preparative chromatography: dissolving the crude extract containing Ergosterol peroxide prepared in step (1) with 60-95% methanol aqueous solution to obtain a first sample solution for preparative chromatography, performing purification by preparative chromatography, collecting a fraction containing Ergosterol peroxide, concentrating the fraction containing Ergosterol peroxide to dryness under reduced pressure to obtain an extractum containing Ergosterol peroxide;

(3) Purification by simulated moving-bed chromatography: dissolving the extractum containing Ergosterol peroxide prepared in step (2) with 60-95% methanol aqueous solution to obtain a second sample solution, injecting the second sample solution into a simulated moving-bed chromatography system for further purification to obtain an extract liquor containing Ergosterol peroxide, concentrating the extract liquor containing Ergosterol peroxide to dryness under reduced pressure, and obtaining a dry extract containing Ergosterol peroxide;

(4) Dissolving the dry extract rich in Ergosterol peroxide prepared in step (3) with ethyl acetate-cyclohexane under heating conditions, transferring a resultant precipitate into an environment at a temperature of 0-8° C. for recrystallization, and filtering and washing the precipitate to obtain Ergosterol peroxide with high purity.

2. The enrichment method of extracting Ergosterol peroxide from sporoderm-broken *Ganoderma lucidum* spore powder according to claim 1, wherein the extraction solvent of percolation or reflux method in step (1) is one of ethyl acetate, ethyl acetate-cyclohexane, or cyclohexane-petroleum ether, or a mixture thereof in any ratio.

3. The enrichment method of extracting Ergosterol peroxide from sporoderm-broken *Ganoderma lucidum* spore powder according to claim 2, wherein for the percolation method in step (1), the immersing time is 24-48 h, the immersing temperature is room temperature, and a percolate is collected at approximate constant speed for 5-10 bed volume.

4. The enrichment method of extracting Ergosterol peroxide from sporoderm-broken *Ganoderma lucidum* spore powder according to claim 2, wherein for the reflux method in step (1), the liquid-solid ratio is 6:1 to 10:1, the extracting time at boiling condition is 1-2 h, the resultant extract liquid is a residue, the residue is repeatedly extracted to produce a plurality of filtrates, and the filtrates are merged with each other.

5. The enrichment method of extracting Ergosterol peroxide from sporoderm-broken *Ganoderma lucidum* spore powder according to claim 1, wherein for step (2), the preparative chromatography column is packed with 30-50 μm octadecylsilyl silica gel, the height of the column is 45 cm, the solid content of the first sample solution is 0.05-0.2 g/mL, the injection rate is 2-5 mL/min and the injection volume is 0.1 bed volume, performing isocratic elution with 60-95% methanol aqueous solution at the rate of 1.2-2.0 bed volume per hour.

6. The enrichment method of extracting Ergosterol peroxide from sporoderm-broken *Ganoderma lucidum* spore powder according to claim 1, wherein for step (3), the solid content of the second sample solution is 0.05-0.2 g/mL, the simulated moving-bed chromatography system uses octadecylsilyl reversed silica gel with particle size of 30-50 μm as packing materials,
wherein the simulated moving-bed chromatography system has 8, 12, or 16 columns equally divided into four areas, the columns connected in series, and having the following system parameters: room temperature, flow rate of injection pump is 3-6 mL/min, flow rate of elution pump is 16-38 mL/min, extraction velocity is 10-23 mL/min, flow rate for raffinate is 9-21 mL/min, and switching time is 10-24 min.

7. The enrichment method of extracting Ergosterol peroxide from sporoderm-broken *Ganoderma lucidum* spore powder according to claim 2, wherein for step (3), the solid content of the second sample solution is 0.05-0.2 g/mL, the simulated moving-bed chromatography system uses octadecylsilyl reversed silica gel with particle size of 30-50 μm as packing materials,
wherein the simulated moving-bed chromatography system has 8, 12, or 16 columns equally divided into four areas, the columns connected in series, and having the following system parameters: room temperature, flow rate of injection pump is 3-6 mL/min, flow rate of elution pump is 16-38 mL/min, extraction velocity is 10-23 mL/min, flow rate for raffinate is 9-21 mL/min, and switching time is 10-24 min.

8. The enrichment method of extracting Ergosterol peroxide from sporoderm-broken *Ganoderma lucidum* spore powder according to claim 3, wherein for step (3), the solid content of the second sample solution is 0.05-0.2 g/mL, the simulated moving-bed chromatography system uses octadecylsilyl reversed silica gel with particle size of 30-50 μm as packing materials,
wherein the simulated moving-bed chromatography system has 8, 12, or 16 columns equally divided into four areas, the columns connected in series, and having the following system parameters: room temperature, flow rate of injection pump is 3-6 mL/min, flow rate of elution pump is 16-38 mL/min, extraction velocity is 10-23 mL/min, flow rate for raffinate is 9-21 mL/min, and switching time is 10-24 min.

9. The enrichment method of extracting Ergosterol peroxide from sporoderm-broken *Ganoderma lucidum* spore powder according to claim 4, wherein for step (3), the solid content of the second sample solution is 0.05-0.2 g/mL, the simulated moving-bed chromatography system uses octadecylsilyl reversed silica gel with particle size of 30-50 μm as packing materials,
wherein the simulated moving-bed chromatography system has 8, 12, or 16 columns equally divided into four areas, the columns connected in series, and having the following system parameters: room temperature, flow rate of injection pump is 3-6 mL/min, flow rate of elution pump is 16-38 mL/min, extraction velocity is 10-23 mL/min, flow rate for raffinate is 9-21 mL/min, and switching time is 10-24 min.

10. The enrichment method of extracting Ergosterol peroxide from sporoderm-broken *Ganoderma lucidum* spore powder according to claim 5, wherein for step (3), the solid content of the second sample solution is 0.05-0.2 g/mL, the simulated moving-bed chromatography system uses octadecylsilyl reversed silica gel with particle size of 30-50 μm as packing materials,
wherein the simulated moving-bed chromatography system has 8, 12, or 16 columns equally divided into four areas, the columns connected in series, and having the following system parameters: room temperature, flow rate of injection pump is 3-6 mL/min, flow rate of elution pump is 16-38 mL/min, extraction velocity is 10-23 mL/min, flow rate for raffinate is 9-21 mL/min, and switching time is 10-24 min.

11. The enrichment method of extracting Ergosterol peroxide from sporoderm-broken *Ganoderma lucidum* spore powder according to claim 1, wherein in step (4), the dosage of ethyl acetate-cyclohexane is 10-20 times that of the dry extract, the volume ratio of ethyl acetate to cyclohexane is 50:50-10:90, and the time of recrystallization is 36-48 h.

12. The enrichment method of extracting Ergosterol peroxide from sporoderm-broken *Ganoderma lucidum* spore powder according to claim 2, wherein in step (4), the dosage of ethyl acetate-cyclohexane is 10-20 times that of the dry extract, the volume ratio of ethyl acetate to cyclohexane is 50:50-10:90, and the time of recrystallization is 36-48 h.

13. The enrichment method of extracting Ergosterol peroxide from sporoderm-broken *Ganoderma lucidum* spore powder according to claim 3, wherein in step (4), the dosage of ethyl acetate-cyclohexane is 10-20 times that of the dry extract, the volume ratio of ethyl acetate to cyclohexane is 50:50-10:90, and the time of recrystallization is 36-48 h.

14. The enrichment method of extracting Ergosterol peroxide from sporoderm-broken *Ganoderma lucidum* spore powder according to claim 4, wherein in step (4), the dosage of ethyl acetate-cyclohexane is 10-20 times that of the dry extract, the volume ratio of ethyl acetate to cyclohexane is 50:50-10:90, and the time of recrystallization is 36-48 h.

15. The enrichment method of extracting Ergosterol peroxide from sporoderm-broken *Ganoderma lucidum* spore powder according to claim 5, wherein in step (4), the dosage of ethyl acetate-cyclohexane is 10-20 times that of the dry extract, the volume ratio of ethyl acetate to cyclohexane is 50:50-10:90, and the time of recrystallization is 36-48 h.

* * * * *